(12) United States Patent
Malenchek

(10) Patent No.: US 6,527,742 B1
(45) Date of Patent: Mar. 4, 2003

(54) SAFETY SYRINGE

(76) Inventor: Robert C. Malenchek, 279 Sunnymead Rd., Hillsborough, NJ (US) 08844

( * ) Notice: Subject to any disclaimer, the term of this patent is extended or adjusted under 35 U.S.C. 154(b) by 0 days.

(21) Appl. No.: 09/992,294

(22) Filed: Nov. 14, 2001

(51) Int. Cl.[7] ............................. A61M 5/00; A61M 5/32
(52) U.S. Cl. ........................................ 604/110; 604/198
(58) Field of Search .................................. 604/110, 192, 604/195, 198, 163, 263, 187, 171

(56) References Cited

U.S. PATENT DOCUMENTS

| | | |
|---|---|---|
| 4,699,614 A | 10/1987 | Glazier |
| 4,801,295 A | 1/1989 | Spencer |
| 4,850,968 A | 7/1989 | Romano |
| 4,850,977 A | 7/1989 | Bayless |
| 4,883,466 A | 11/1989 | Glazier |
| 4,900,311 A | 2/1990 | Stern et al. |
| 4,911,693 A | 3/1990 | Paris |
| 4,927,416 A | 5/1990 | Tomkiel |
| 4,929,237 A | 5/1990 | Medway |
| 4,932,940 A | 6/1990 | Walker et al. |
| 4,932,947 A | 6/1990 | Cardwell |
| 4,946,446 A | 8/1990 | Vadher |
| 4,955,868 A | 9/1990 | Klein |
| 4,966,592 A | 10/1990 | Burns et al. |
| 4,973,316 A | 11/1990 | Dysarz |
| 4,978,343 A | 12/1990 | Dysarz et al. |
| 5,013,301 A | 5/1991 | Marotta, Jr. et al. |
| 5,019,051 A | 5/1991 | Hake |
| 5,026,354 A | 6/1991 | Kocses |
| 5,049,133 A | 9/1991 | Villen Pascual |
| 5,049,136 A | 9/1991 | Johnson |
| 5,053,018 A | 10/1991 | Talonn et al. |
| 5,057,079 A | 10/1991 | Tiemann et al. |
| 5,066,277 A | 11/1991 | Carrell et al. |
| 5,088,986 A | 2/1992 | Nusbaum |
| 5,088,988 A | 2/1992 | Talonn et al. |
| 5,112,307 A | 5/1992 | Haber et al. |
| 5,127,910 A | 7/1992 | Talonn et al. |
| 5,147,303 A | 9/1992 | Martin |
| 5,147,326 A | 9/1992 | Talonn et al. |
| 5,160,326 A | 11/1992 | Talonn et al. |
| 5,180,370 A | 1/1993 | Gillespie |
| 5,273,541 A | 12/1993 | Malenchek |
| 5,279,584 A | 1/1994 | Dillard, III et al. |
| 5,312,347 A | 5/1994 | Osborne et al. |
| 5,312,370 A | 5/1994 | Talonn et al. |
| 5,314,414 A | 5/1994 | Hake et al. |
| 5,318,536 A | 6/1994 | Martin |
| 5,338,304 A | 8/1994 | Adams |
| 5,338,311 A | 8/1994 | Mahurkar |
| 5,346,480 A | 9/1994 | Hess et al. |
| 5,383,863 A | 1/1995 | Mardones |

(List continued on next page.)

FOREIGN PATENT DOCUMENTS

| | | |
|---|---|---|
| EP | 0506204 | 9/1992 |
| GB | 2243552 | 11/1991 |
| GB | 2283683 | 5/1995 |
| WO | 9006148 | 6/1990 |
| WO | 9325254 | 12/1993 |

*Primary Examiner*—Anhtuan T. Nguyen
*Assistant Examiner*—Matthew DeSanto
(74) *Attorney, Agent, or Firm*—Selitto, Behr & Kim

(57) ABSTRACT

A safety syringe is provided which includes a housing and a barrel mounted for reciprocating movement within the housing. A ring is mounted to the barrel and is rotatable relative to the housing and to the barrel. The ring includes a plurality of tabs circumferentially spaced from each other. An interior wall of the housing includes a plurality of ramps and a plurality of stops. The ramps cooperate with the tabs of the ring so as to rotate the ring relative to the housing and to the barrel, while the stops cooperate with the tabs for stopping the rotation of the ring relative to the housing and to the barrel. Locking means is also included within the interior wall of the housing for locking the barrel so as to allow for only a single use of the safety syringe.

38 Claims, 11 Drawing Sheets

U.S. PATENT DOCUMENTS

| | | |
|---|---|---|
| 5,389,085 A | 2/1995 | D'Alessio et al. |
| 5,403,286 A | 4/1995 | Lockwood, Jr. |
| 5,403,287 A | 4/1995 | Talonn et al. |
| 5,411,487 A | 5/1995 | Castagna |
| 5,415,645 A | 5/1995 | Friend et al. |
| 5,417,660 A | 5/1995 | Martin |
| 5,429,612 A | 7/1995 | Berthier |
| 5,429,613 A | 7/1995 | D'Amico |
| 5,433,712 A | 7/1995 | Stiles et al. |
| 5,437,639 A | 8/1995 | Malenchek |
| 5,445,620 A | 8/1995 | Haber et al. |
| 5,472,430 A | 12/1995 | Vaillancourt et al. |
| 5,478,314 A | 12/1995 | Malenchek |
| 5,484,421 A | 1/1996 | Smocer |
| 5,492,536 A | 2/1996 | Mascia |
| 5,498,243 A | 3/1996 | Vallelunga et al. |
| 5,512,050 A | 4/1996 | Caizza et al. |
| 5,549,558 A | 8/1996 | Martin |
| 5,554,122 A | 9/1996 | Emanuel |
| 5,554,130 A | 9/1996 | McDonald et al. |
| 5,562,626 A | 10/1996 | Sanpietro |
| 5,573,513 A | 11/1996 | Wozencroft |
| 5,591,138 A | 1/1997 | Vaillancourt |
| 5,634,903 A | 6/1997 | Kurose et al. |
| 5,643,222 A | 7/1997 | Mahurkar |
| 5,647,849 A | 7/1997 | Kalin |
| 5,688,241 A | 11/1997 | Asbaghi |
| 5,713,873 A | 2/1998 | Jehle |
| 5,735,823 A | 4/1998 | Berger |
| 5,779,683 A * | 7/1998 | Meyer ........................ 604/198 |
| 5,843,041 A | 12/1998 | Hake et al. |
| 5,980,494 A | 11/1999 | Malenchek et al. |
| 5,984,899 A | 11/1999 | D'Alesio et al. |
| 6,015,396 A | 1/2000 | Buttgen et al. |
| 6,083,199 A | 7/2000 | Thorley et al. |
| 6,183,446 B1 | 2/2001 | Jeanbourquin |
| 6,206,853 B1 | 3/2001 | Bonnet |

* cited by examiner

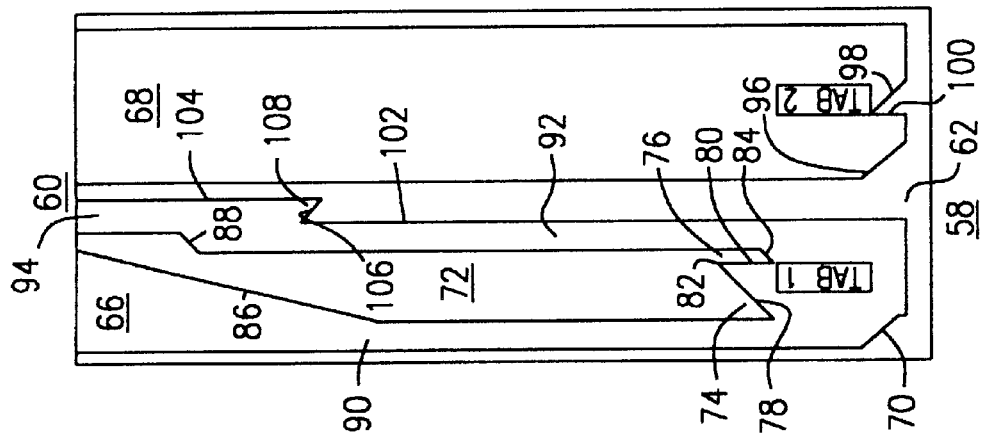
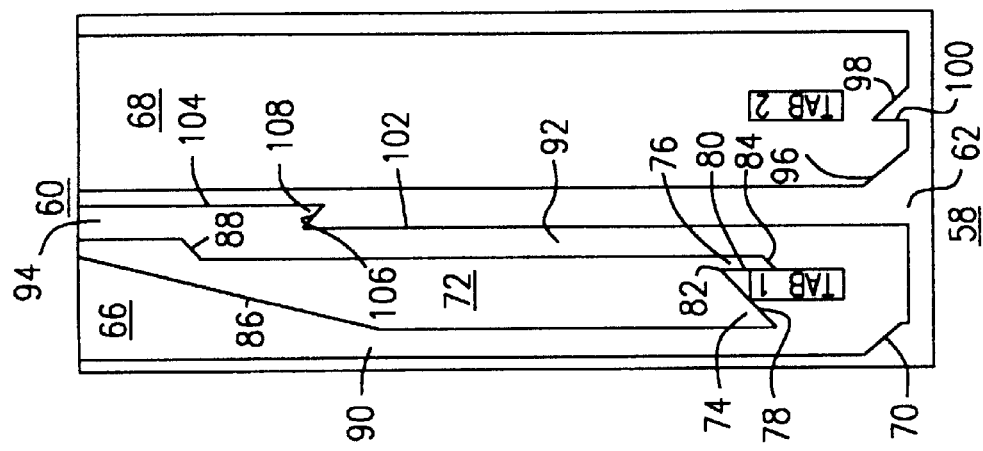

SAFETY SYRINGE

FIELD OF THE INVENTION

The present invention relates to a safety syringe, and, more particularly, to a single use safety syringe.

BACKGROUND OF THE INVENTION

In general, safety syringes include a barrel which has a cavity for storing a desired fluid, a needle assembly which includes a needle and which is secured to the barrel, and a plunger which is selectively inserted or removed from the cavity. Safety syringes may also include a housing which secures the needle therein.

Various mechanisms have been proposed to allow the needle to be temporarily secured in the housing prior to use of the safety syringe and to be permanently locked therein after use of the safety syringe so as to prevent further use of the safety syringe and to prevent needle pricks. For example, U.S. Pat. No. 5,980,494 discloses an exemplary safety syringe that automatically extends a needle from a housing and retracts the needle into the housing upon axial displacement of its barrel.

Although the syringe disclosed in the '494 Patent is effective for its intended use, there is a need for a novel safety syringe which is particularly suitable for small dose injections (e.g., an insulin injection). Because such syringes are sized and shaped to allow for only a single use thereof, they typically have a relatively small size (e.g., 1 cc). Due to safety concerns, these syringes, like their larger counterparts, should prevent needle pricks and should be relatively inexpensive to manufacture.

SUMMARY OF THE INVENTION

In accordance with the present invention, a safety syringe is disclosed which includes a housing having a bore which extends from a distal end of the housing to a proximal end thereof. The safety syringe also includes a barrel being mounted for reciprocating movement within the housing such that the barrel is movable between a retracted position and an extended position. A ring is mounted to the barrel and is rotatable relative to the housing and to the barrel. The ring includes a plurality of tabs circumferentially spaced from each other. Urging means is also provided for urging the barrel toward its retracted position.

An interior wall of the housing includes a plurality of ramp means and a plurality of stop means. The ramp means is provided for rotating the ring relative to the housing and to the barrel, while the stop means is provided for stopping the rotation of the ring relative to the housing and to the barrel. Locking means is also included within the interior wall of the housing for locking the barrel in its retracted position.

In accordance with one embodiment, the interior wall of the housing includes a plurality of ramps, each of which being sized and shaped so as to allow one of the tabs to slide therealong. The interior wall of the housing also includes a plurality of stops, each of which positioned so as to be engageable by one of the tabs.

Other features and aspects of the present invention will become more fully apparent from the following detailed description of an exemplary embodiment, the appended claims and the accompanying drawings.

BRIEF DESCRIPTION OF THE DRAWINGS

For a more complete understanding of the present invention, reference is made to the following detailed description of an exemplary embodiment considered in conjunction with the accompanying drawings, in which:

FIGS. 7–19 are sequential views similar to the view shown in FIG. 6, schematically illustrating ring tabs of the ring shown in FIG. 4 in various positions along the interior of the shield illustrated in FIG. 6.

DETAILED DESCRIPTION OF THE EXEMPLARY EMBODIMENT

Figure 1:
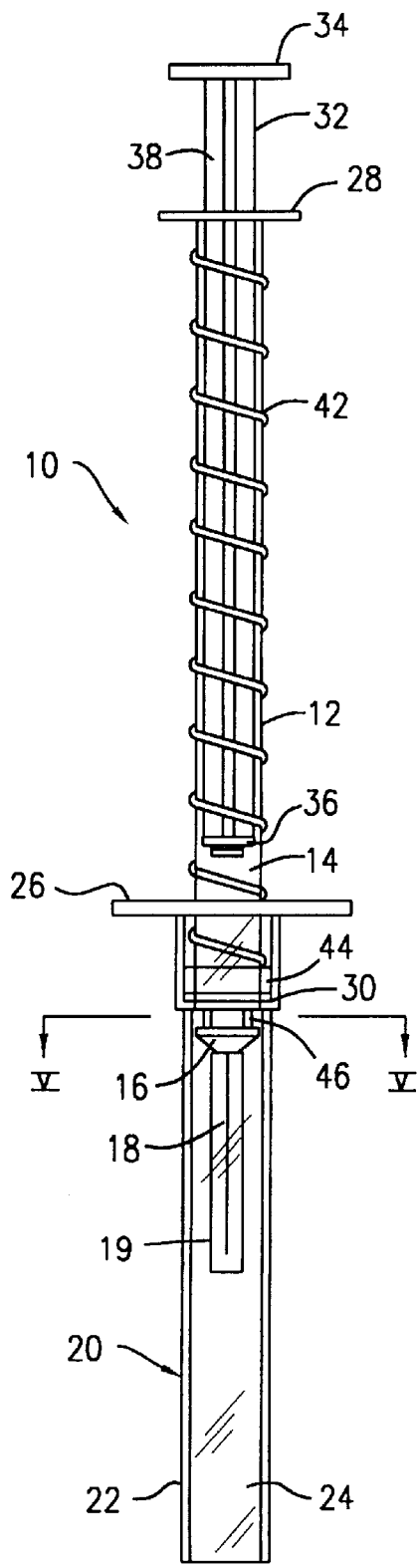
FIG. 1 is an elevational view of a safety syringe constructed in accordance with the present invention, which shows a barrel in a retracted position.
Figure 2:
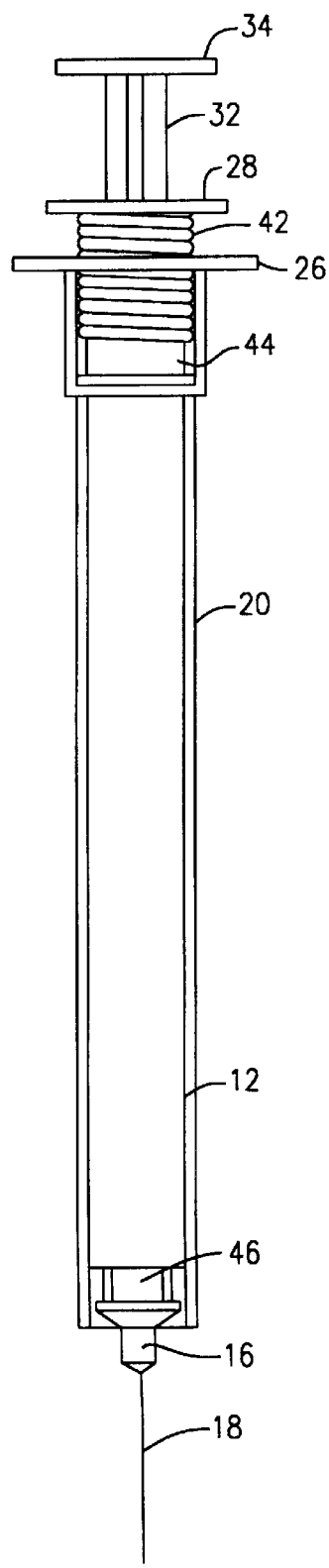
FIG. 2 is an elevational view similar to that of FIG. 1, except that the barrel is in an extended position.
Figure 3:
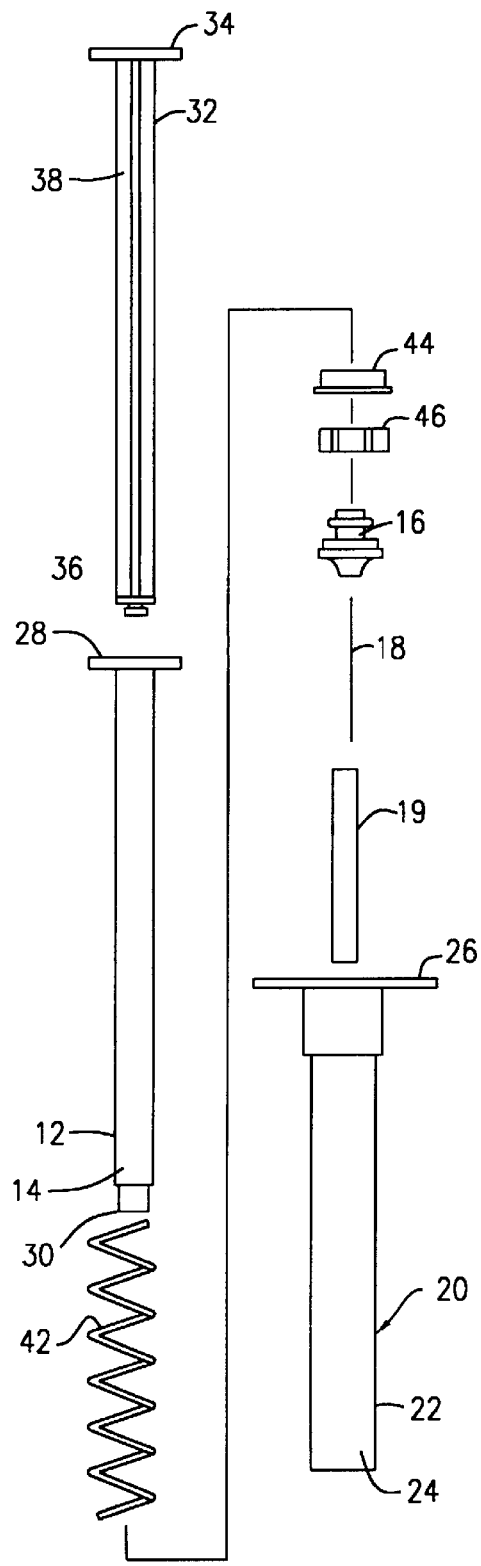
FIG. 3 is an exploded view of the safety syringe illustrated in FIGS. 1–2.

FIGS. 1–3 illustrate a safety syringe 10 constructed in accordance with the present invention. Although the safety syringe 10 is suitable for dose injections of any size, it is particularly suitable for small dose injections, wherein a 1 cc syringe is required.

With reference to FIGS. 1–3, the safety syringe 10 includes a polypropylene molded barrel 12 having a cavity 14 for storing a desired fluid (e.g., insulin) and a needle assembly 16 releaseably secured to the barrel 12. The needle assembly 16 includes a needle 18 attached thereto and a cover 19 for the needle 18.

A polypropylene molded shield 20 is sized and shaped so as to allow the barrel 12 to be temporarily secured therein. More particularly, the shield 20 has a cylindrical body 22 with a cylindrical bore 24, as well as a finger gripping flange 26. The bore 24 extends from a distal end of the shield 20 to a proximal end of the shield 20.

As illustrated in FIGS. 1–3, the barrel 12 includes a flange 28 located on a proximal end thereof, and a mounting surface 30 located on a distal end thereof. The barrel 12 is mounted for reciprocating movement within the shield 20 such that the barrel 12 is movable between a retracted position (see FIG. 1), in which position the needle 18 retracts into the shield 20, and an extended position (see FIG. 2), in which position the needle 18 extends from the shield 20. As illustrated in FIGS. 1 and 2, the mounting surface 30 of the barrel 12 is located proximate the proximal end of the shield 20 when the barrel 12 is in its retracted position, and is located proximate the distal end of the shield 20 when the barrel 12 is in its extended position.

Still referring to FIGS. 1–3, the safety syringe 10 includes a plunger 32 which is selectively inserted into and removed from the cavity 14 of the barrel 12. More particularly, the plunger 32 includes a finger gripping flange 34 on one end, a sealing flange 36 on an opposite end, and a shaft 38 which connects the flanges 34, 36. The sealing flange 36 is sized and shaped so as to prevent leakage of fluid from the cavity 14 of the barrel 12. As will be described in greater detail hereinafter, the plunger 32 is mounted for reciprocating movement within the barrel 12 so as to move the barrel 12 to its extended position (see FIG. 2) when the flange 34 of the plunger 32 is pushed axially toward the shield 20.

Urging means, such as a helical compression spring 42 (see FIGS. 1–3), is mounted about the barrel 12. The spring 42 extends between the flange 28 of the barrel 14 and the distal end of the barrel 14. A substantial portion of the spring 42 is located externally of the shield 20 when the barrel 12 is in its retracted position. The spring 42 is sized and shaped so as to axially urge the barrel 12 to its retracted position (see FIG. 1), in which position the spring 42 is compressed to about twenty-four percent of its total possible compression. When the barrel 12 is in its extended position (see FIG. 2), the spring 42 is compressed to about ninety-six percent of its total possible compression. The spring 42 is designed to generate axial tension force, as well as rotational tension force.

With reference to FIGS. 1–3, the safety syringe 10 further includes a polypropylene molded retaining bushing 44 mounted to the shield 20. The retaining bushing 44 is sized and shaped so as to prevent removal of the safety syringe components during use of the safety syringe 10.

Figure 4:
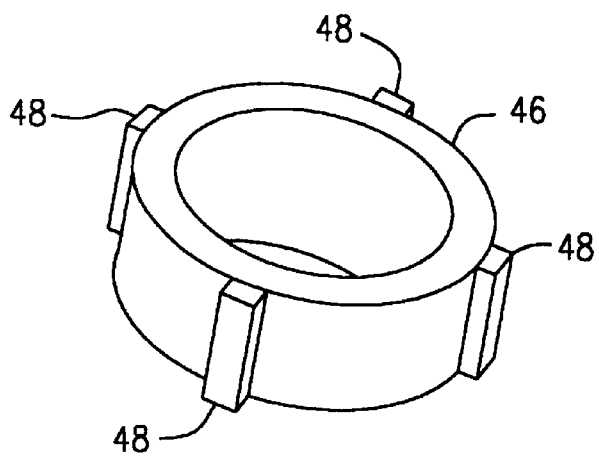
FIG. 4 is a perspective view of a ring used in the safety syringe illustrated in FIGS. 1–3.
Figure 7:
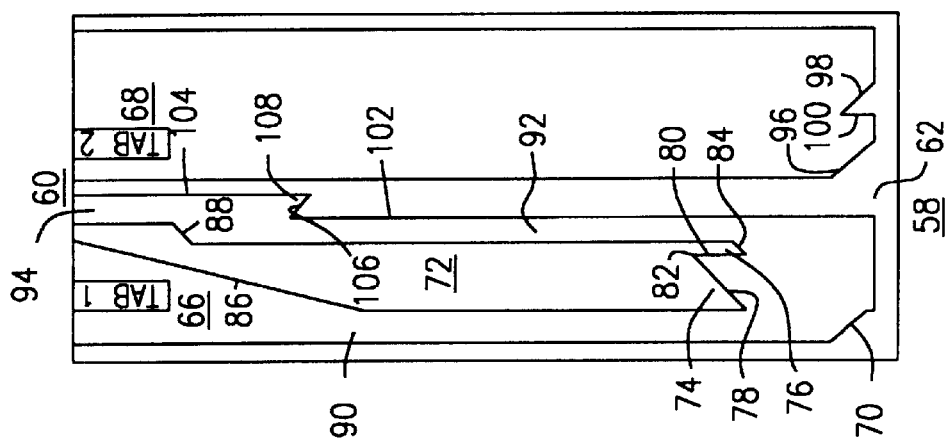

As illustrated in FIG. 4, a cylindrical, polypropylene molded ring 46 is provided with four external tabs 48 (two of which are schematically illustrated in FIG. 7 as "TAB 1" and "TAB 2", respectively). The four tabs 48 are circumferentially spaced, at equal intervals, around the exterior of the ring 46. Referring back to FIGS. 1 and 3, the ring 46 is secured to the mounting surface 30 of the barrel 12 such that the tabs 48 can rotate about the mounting surface 30 and can be axially displaced along the mounting surface 30. The ring 46 is sized and shaped so as to be rotatable relative to the shield 20 and to the barrel 12. As will be described in greater detail hereinafter, the tabs 48 are sized and shaped so as to position the ring 46 in various positions relative to the shield 20 and to the barrel 12.

Figure 5:
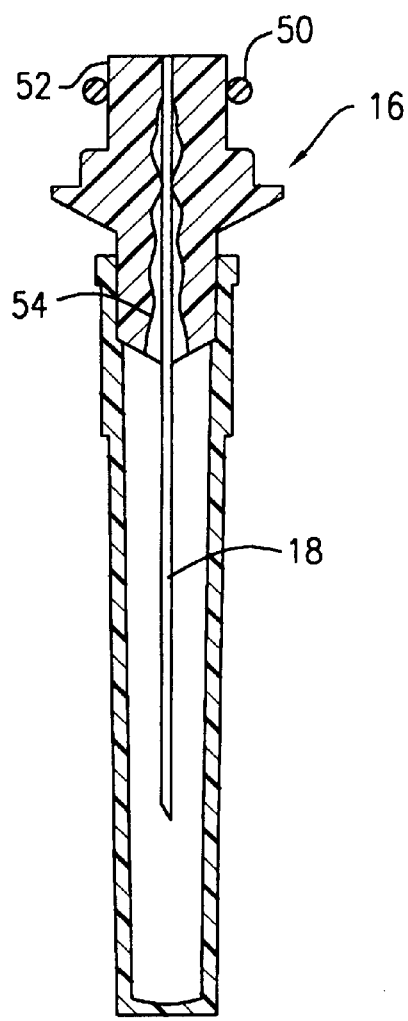
FIG. 5 is a cross-sectional view, taken along section line V—V and looking in the direction of the arrows, of a needle assembly used in the safety syringe illustrated in FIG. 1.

With reference to FIG. 5, the needle assembly 16 is sized and shaped so as to secure the ring 46 to the barrel 12. More particularly, an O-ring 50 is molded into the needle assembly 16 and is used to seal the needle assembly 16 to the barrel 12. A mating surface 52 is included below the O-ring 50 and serves to retain the needle assembly 16 in the barrel 12. The needle assembly 16 includes an adhesive 54 (e.g., an UW-Cure adhesive) which forms a mechanical bond therewith by the use of decreasing undercuts, and which is used to retain the needle 18 within the needle assembly 16.

Figure 6:
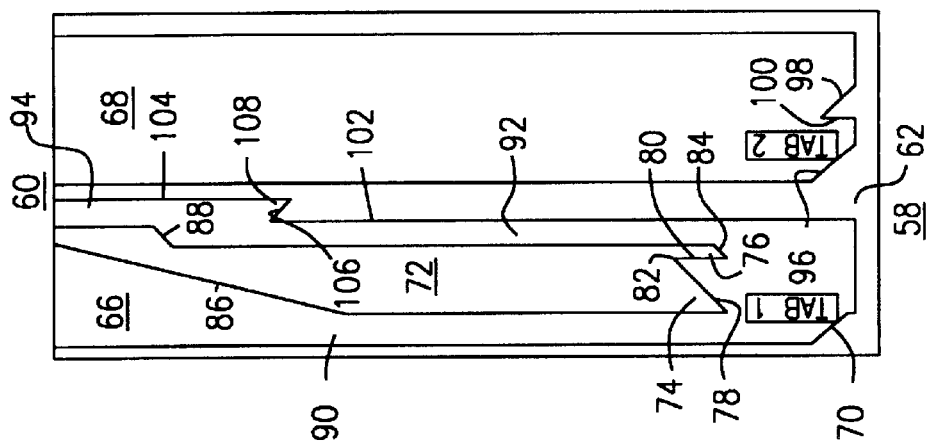
FIG. 6 is a fragmentary flattened view of an interior of a shield used in the safety syringe illustrated in FIGS. 1–3.

Referring to FIG. 6, an interior wall 56 of the shield 20 is illustrated in a flattened position. The shield 20 has an end 58 distal to its flange 26 and an end 60 proximal thereto. The interior wall 56 of the shield 20 includes a raised segment 62 which extends along a longitudinal axis 64 and along the circumference of the shield 20 at the distal end 58. As illustrated in FIG. 6, the raised segment 62 has a plurality of open areas 66, 68 circumferentially spaced from each other. Although only one set of the foregoing features is illustrated in FIG. 6, the interior wall 56 can be formed with two or more sets.

Still referring to FIG. 6, the raised segment 62 has first ramp means, such as a lower angled surface 70, protruding into the open area 66 and being sized and shaped so as to allow "TAB 1" (see FIG. 7) to slide therealong. The lower angled surface 70 is located proximate the distal end 58 of the shield 20.

The open area 66 includes a raised segment 72 having a distal edge in the form of ratchet teeth 74, 76. More particularly, the tooth 74 has second ramp means, such as an inclined edge 78, which is sized and shaped so as to allow "TAB 1" (see FIG. 7) to slide therealong. The other tooth 76 has first stop means, such as an axially extending linear edge 80, positioned adjacent to the inclined edge 78 so as to form a V-shaped trough 82 between the ratchet teeth 74, 76. The V-shaped trough 82 is sized and shaped so as to temporarily lock "TAB 1" (see FIG. 7) of the ring 46 therein as will be explained in further detail hereinafter.

Both the inclined edge 78 and the linear edge 80 of the ratchet teeth 74, 76 protrude into the open area 66 and are located intermediate the lower angled surface 70 of the raised segment 62 and the proximal end 60 of the shield 20. The tooth 76 also includes guiding means, such as a lower lock ramp 84, which protrudes into the open area 66 and which is positioned adjacent the linear edge 80 of the ratchet tooth 76. The raised segment 72 has a proximal edge in the form of an inclined surface 86 on one side and an upper lock ramp 88 on an opposite side.

A linearly extending assembly groove 90 is formed on one side of the raised segment 72. The assembly groove 90 extends from the proximal end 60 of the shield 20 to the distal end 58 thereof, and is sized and shaped so as to slidably receive "TAB 1" (see FIG. 7).

A lower lock groove 92 and an upper lock groove 94 are formed on an opposite side of the raised segment 72.

Both the lower lock groove 92 and the upper lock groove 94 extend from the proximal end 60 of the shield 20 to the distal end 58 thereof, and are sized and shaped so as to slidably receive "TAB 1" (see FIG. 7).

The open area 68 extends from the proximal end 60 of the shield 20 to the distal end 58 thereof, and is sized and shaped so as to slidably receive "TAB 2" (see FIG. 7). Third ramp means, such as a lower angled surface 96, of the raised segment 62 protrudes into the open area 68, and is sized and shaped so as to allow "TAB 2" to slide therealong. The lower angled surface 96 is located proximate the distal end 58 of the shield 20.

The raised segment 62 has fourth ramp means, such as an inclined surface 98, which is sized and shaped so as to allow "TAB 2" (see FIG. 7) to slide therealong. An axially extending linear edge 100 is positioned adjacent the inclined surface 98. Both the inclined surface 98 and the axially extending linear edge 100 protrude into the open area 68 and are positioned adjacent the distal end 58 of the shield 20.

The raised segment 62 includes third stop means, such as a linearly extending wall 102, formed adjacent one side of the open area 66. Another linearly extending wall 104 is located proximal to the wall 102. More particularly, the wall 104 is spaced further from the raised segment 72 than the wall 102.

The raised segment 62 also includes locking means, such as an intermediate lock ramp 106 extending between the walls 102, 104 so as to form a V-shaped notch 108. As illustrated in FIG. 6, the V-shaped notch 108 protrudes outwardly from the open area 66 and is sized and shaped so as to be engageable by "TAB 1" (see FIG. 7).

In operation, the barrel 12 is initially in the retracted position (see FIG. 1), the spring 42 is initially substantially fully extended, and the ring 46 is positioned adjacent the retaining bushing 44 (see FIG. 1). The safety syringe 10 is delivered to a user in this position. FIG. 7 shows "TAB 1" initially positioned in the assembly groove 90 at the proximal end 60 of the shield 20, and shows "TAB 2" positioned in the open area 68 at the proximal end 60.

Figure 8:
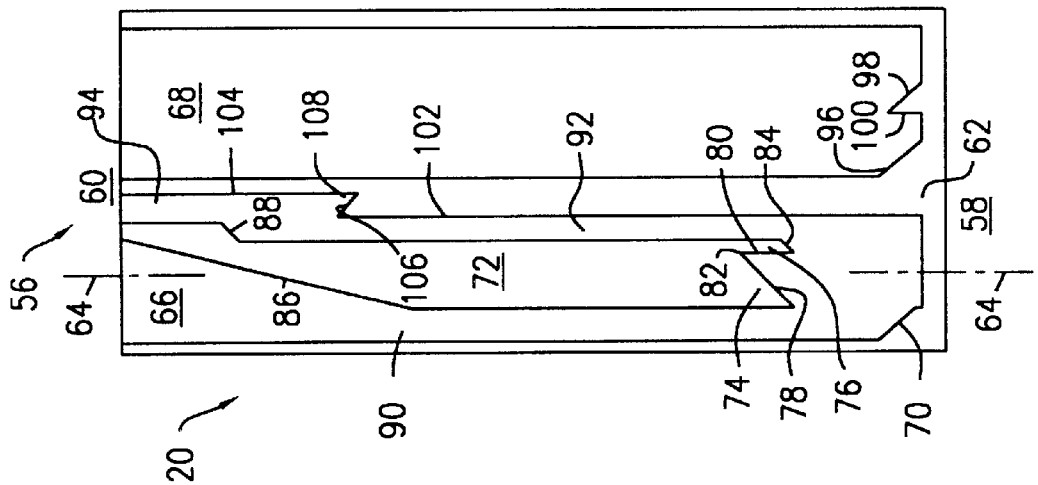
Figure 9:
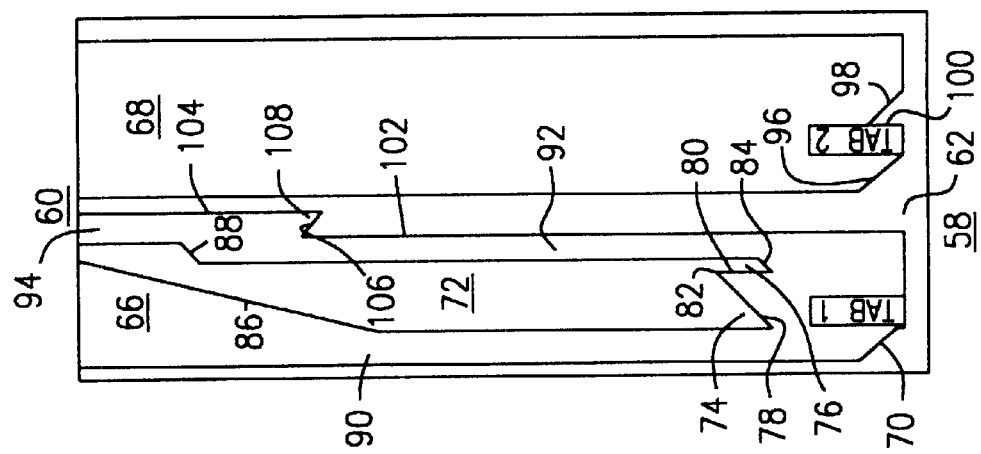

Referring now to FIG. 8, the barrel 12 is displaced toward its extended position (see FIG. 2) as the plunger 32 is pushed axially toward the distal end 58 of the shield 20. As the barrel 12 moves toward its extended position, the spring 42 compresses and the ring 46 moves toward the distal end 58 of the shield 20. In turn, "TAB 1" contacts the lower angled surface 70, which protrudes into the open area 66, while "TAB 2" contacts the lower angled surface 96, which protrudes into the open area 68. As "TAB 1" slides along the lower angled surface 70 and "TAB 2" slides along the lower angled surface 96, the ring 46 is rotated relative to the shield 20 to a position illustrated in FIG. 9. When "TAB 2" engages the linear edge 100, "TAB 1" ceases to rotate and is axially aligned with the inclined edge 78 of the tooth 74. Also, when "TAB 2" engages the linear edge 100, the ring 46 ceases to rotate relative to the shield 20 and to the barrel 12. For manufacturing reasons, the final few degrees that the ring 46 rotates, is actuate d by the lower angled surface 96, which protrudes into the open area 68, rather than by the lower angled surface 70, which protrudes into the open area 66.

Figure 10:
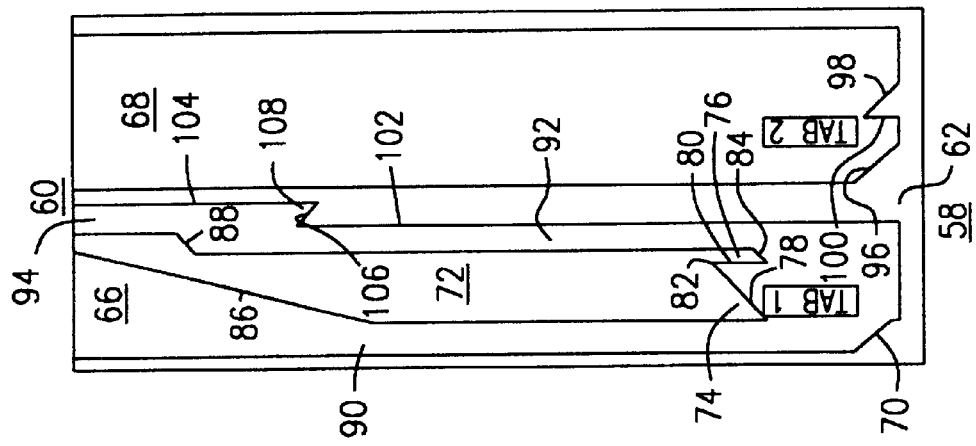

Referring now to FIG. 10, upon release of the plunger 32, the spring 42 urges the barrel 12 toward the proximal end 60, thereby moving the ring 46 in the same direction such that "TAB 1" contacts the inclined edge 78 of the ratchet tooth 74. It should be noted that "TAB 2" has also moved toward the proximal end 60, but is not performing any function at this point. The spring 42 continues to move the ring 46 toward the proximal end 60 such that "TAB 1" slides along the inclined edge 78 of the ratchet tooth 74 until it engages the linear edge 80 of the ratchet tooth 76, thereby rotating the ring 46 to a position illustrated in FIG. 11. As the ring 46 rotates, "TAB 2" rotates in the same direction to a position in which it is axially aligned with the inclined surface 98.

In the position illustrated in FIG. 11, "TAB 1" is temporarily locked in the V-shaped trough 82 such that it cannot rotate any further, thereby ceasing the rotation of the ring 46 and temporarily locking the barrel 12 in place. Once the barrel 12 is temporarily locked in place, the safety syringe 10 is ready for use.

To use the safety syringe 10, the needle 18 is first exposed by removing the cover 19 therefrom. Then, the plunger 32 is used to place the desired fluid in the cavity 14 (see FIG. 1) of the barrel 12 by withdrawing the plunger 32 in a direction away from the shield 20 so as to create a vacuum in the cavity 14 as is known in the art. The plunger 32 is then depressed to inject the fluid in a conventional manner.

Figure 13:
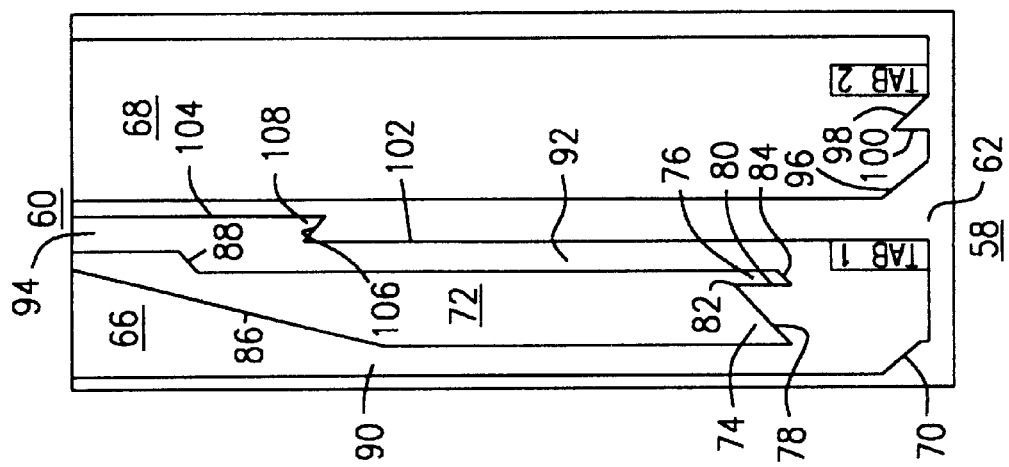

After use, the safety syringe 10 can be locked in a safety position, in which position the needle 18 is permanently locked inside the shield 20 so as to prevent needle pricks. To place the safety syringe 10 in the safety position, the plunger 32 is pressed to thereby urge the barrel 12 toward the distal end 58, thereby moving the ring 46 in the same direction such that "TAB 2" contacts the inclined surface 98 as illustrated in FIG. 12. As "TAB 2" slides along the inclined surface 98, "TAB 1" engages the wall 102 so as to be axially aligned with the lower lock groove 92 and the ring 46 rotates to a position illustrated in FIG. 13. When "TAB 1" contacts the wall 102, the ring 46 ceases to rotate relative to the shield 20. It will be understood that "TAB 2" will not perform any further function from this point on.

Figure 14:
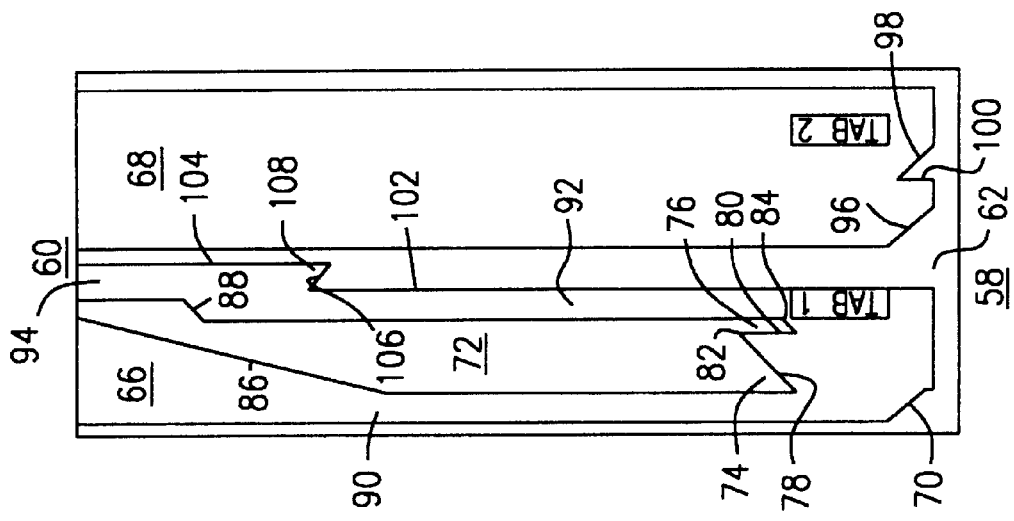
Figure 16:
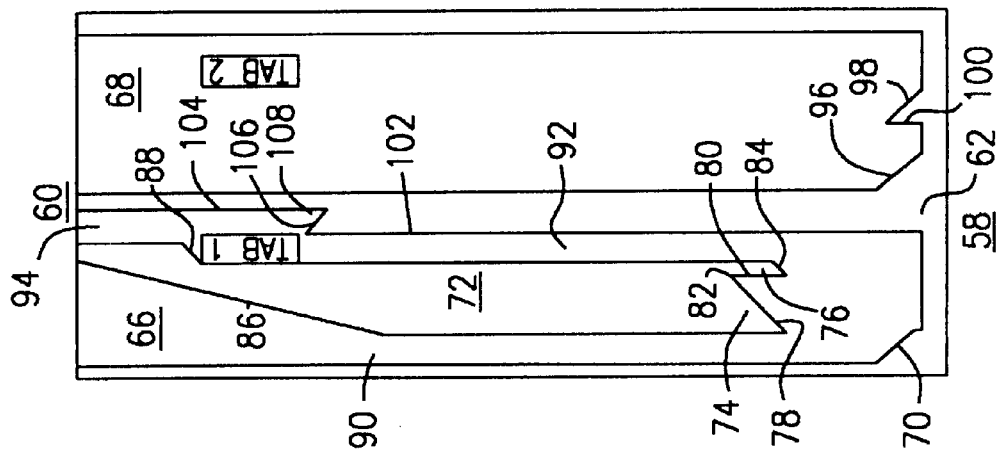
Figure 15:
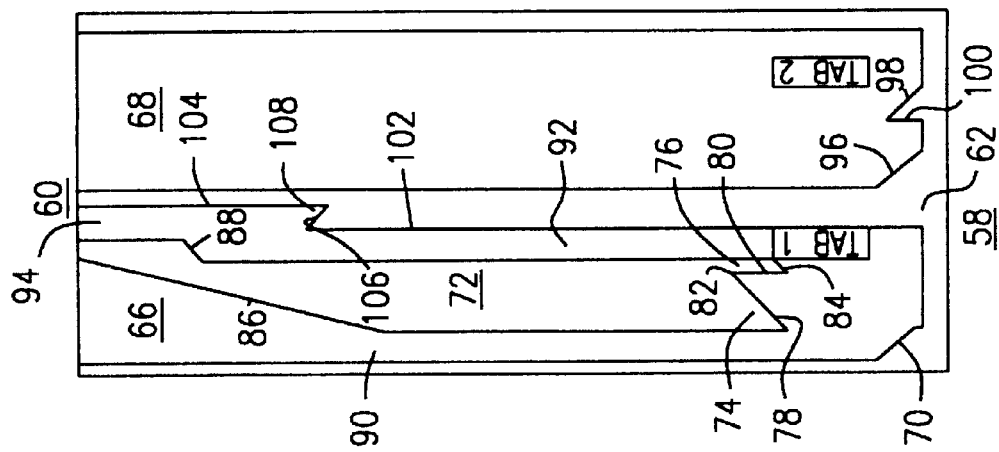

Referring now to FIG. 14, upon release of the plunger 32, the spring 42 urges the barrel 12 toward the proximal end 60, thereby moving the ring 46 in the same direction such that "TAB 1" contacts the lower lock ramp 84 of the ratchet tooth 76. The spring 42 continues to move the ring 46 toward the proximal end 60 such that "TAB 1" is guided by the lower lock ramp 84, rotating the ring 46 to a position illustrated in FIG. 15. In this position, the spring 42 urges the barrel 12 to its retracted position (see FIG. 1), thereby moving the ring 46 toward the proximal end 60 such that "TAB 1" traverses the lower lock groove 92 until it contacts the upper lock ramp 88 of the raised segment 62 as illustrated in FIG. 16.

Figure 18:
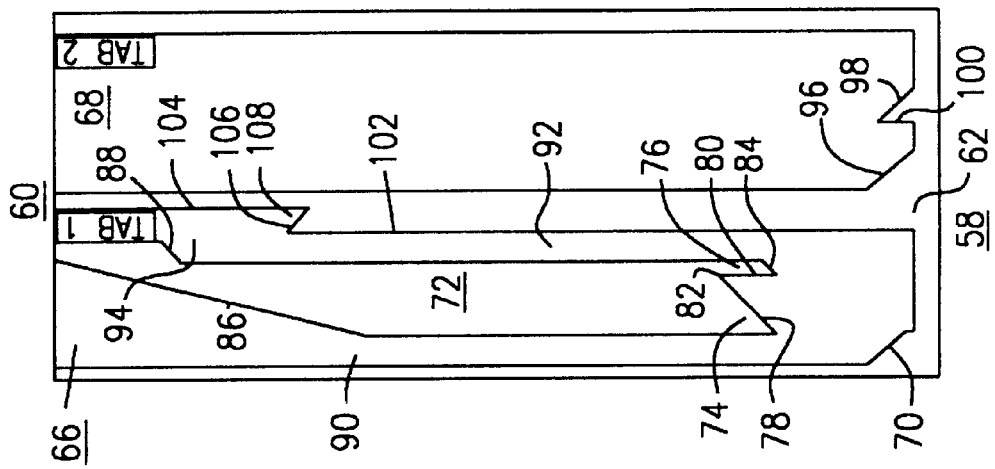
Figure 17:
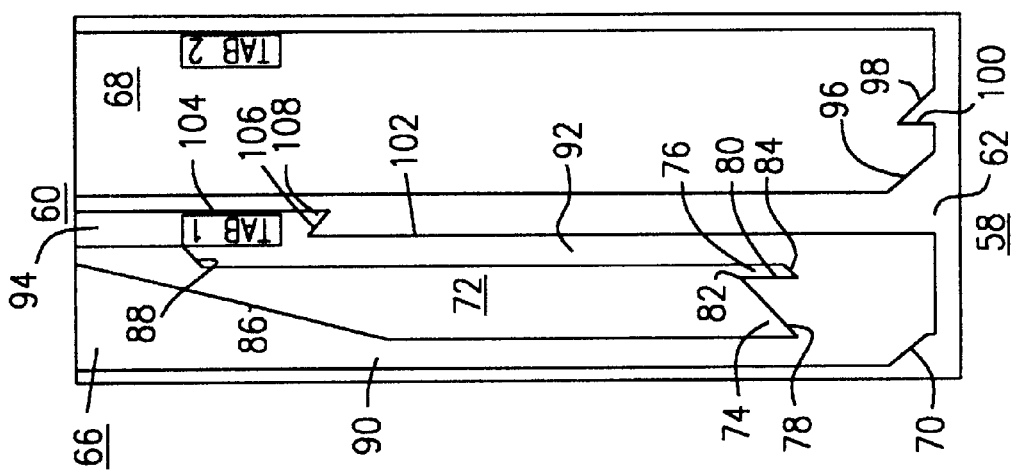

The force of the spring 42 causes the ring 46 to move toward the proximal end 60 such that "TAB 1" slides along the upper lock ramp 88, rotating the ring 46 to a position illustrated in FIG. 17. Referring now to FIG. 18, the force of the spring 42 continues to move the ring 46 toward the proximal end 60 such that "TAB 1" and "TAB 2" are finally adjacent the retaining bushing 44. This places the safety syringe 10 in the safety position, in which it can be disposed of in a normal manner.

Figure 19:
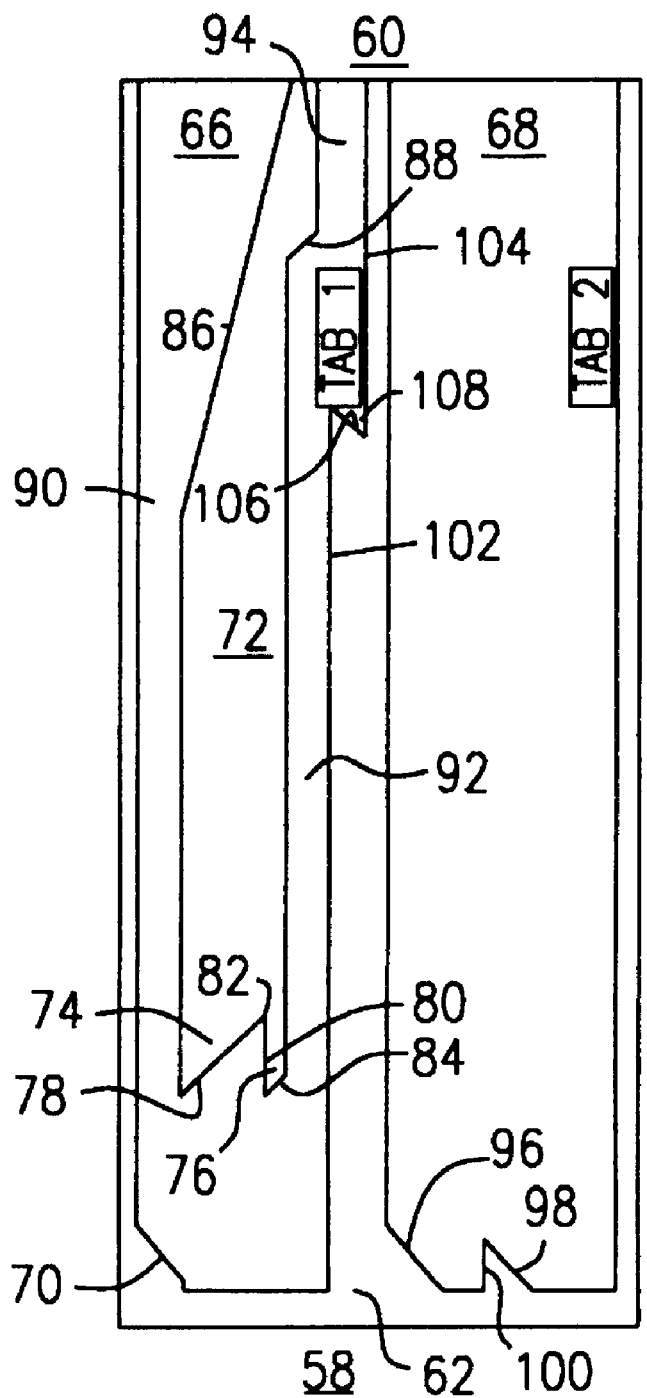

Referring now to FIG. 19, if the user attempts to reuse the safety syringe 10 by depressing the plunger 32, the barrel 12 will move toward the distal end 58, thereby moving the ring 46 in the same direction such that "TAB 1" engages the V-shaped notch 108. The V-shaped notch 108 is sized and shaped such that it precludes lateral movement of "TAB 1", thereby permanently locking the barrel 12 in its retracted position such that the needle 18 is permanently concealed in the shield 20.

As is evident from the foregoing description, the safety syringe 10 is sized and shaped so as to allow for only a single use thereof, and includes a safety feature so as to prevent needle pricks. The safety syringe 10 is also particularly suitable for small dose injections and is relatively inexpensive to manufacture.

The safety syringe 10 can have numerous modifications and variations. For example, if the plunger 32 is not used, the barrel 12 can be placed in the extended position (see FIG. 2) by pushing the flange 28 of the barrel 12 axially toward the shield 20. Although the barrel 12, the ring 46, the shield 20, and the retaining bushing 44 are molded of polypropylene, other materials can be used besides polypropylene.

It will be understood that the embodiment described herein is merely exemplary and that a person skilled in the art may make many variations and modifications without departing from the spirit and scope of the invention. All such variations and modifications, including those discussed above, are intended to be included within the scope of the invention as defined in the appended claims.

The invention claimed is:

1. In a safety syringe which includes a housing having a bore which extends from a distal end of said housing to a proximal end of said housing; a barrel having a distal end located in said housing and a proximal end located externally of said housing, said barrel being mounted for reciprocating movement within said housing such that said barrel is movable between a retracted position, in which said distal end of said barrel is located proximate said proximal end of said housing, and an extended position, in which said distal end of said barrel is located proximate said distal end of said housing; a needle assembly attached to said barrel at said distal end thereof, said needle assembly having a needle attached thereto; a ring mounted to said barrel about said distal end thereof, said ring being rotatable relative to said housing and to said barrel and including a first tab and a second tab circumferentially spaced from said first tab; and urging means for urging said barrel toward its said retracted position, the improvement wherein said housing has an interior wall which includes a first raised segment having a first open area and a second open area circumferentially spaced from said first open area, said first raised segment having a first ramp which protrudes into said first open area and which is sized and shaped so as to allow said first tab to slide therealong, said first open area including a second raised segment having a second ramp, which protrudes into said first open area and which is sized and shaped so as to allow said first tab to slide therealong, and a first stop, which protrudes into said first open area and which is positioned adjacent said second ramp, said second raised segment being sized and shaped so as to form a first groove on one side thereof and a second groove on an opposite side thereof, said first groove extending from said proximal end of said housing to said distal end of said housing and being sized and shaped so as to slidably receive said first tab, said second groove extending from said proximal end of said housing to said distal end of said housing and being sized and shaped so as to slidably receive said first tab, said second open area extending from said proximal end of said housing to said distal end of said housing and being sized and shaped so as to slidably receive said second tab, said first raised segment having a third ramp, which protrudes into said second open area and which is sized and shaped so as to allow said second tab to slide therealong, a fourth ramp, which protrudes into said second open area and which is sized and shaped so as to allow said second tab to slide therealong, a second stop, which protrudes into said second open area and which is positioned adjacent said fourth ramp, and locking means, positioned so as to be engageable by said first tab, for locking said barrel in its said retracted position such that said needle is concealed in said housing.

2. The improved safety syringe of claim 1, wherein said urging means is a compression spring mounted about said barrel such that a substantial portion of said compression spring is located externally of said housing when said barrel is in its said retracted position.

3. The improved safety syringe of claim 2, wherein said barrel includes a flange positioned at said proximal end thereof, said compression spring extending between said flange and said distal end of said barrel.

4. The improved safety syringe of claim 1, further including a plunger mounted for reciprocating movement within said barrel so as to move said barrel to its said extended position.

5. The improved safety syringe of claim 1, wherein said locking means includes a V-shaped notch protruding outwardly from said first open area, said V-shaped notch being sized and shaped so as to preclude lateral movement of said first tab.

6. The improved safety syringe of claim 1, wherein said second raised segment includes guiding means for guiding said first tab into said second groove.

7. The improved safety syringe of claim 6, wherein said guiding means includes a lock ramp, which protrudes into said first open area and which is positioned adjacent said first stop.

8. The improved safety syringe of claim 1, wherein said first raised segment further includes a third stop formed adjacent one side of said first open area.

9. The improved safety syringe of claim 8, wherein said first ramp of said first raised segment is located proximate said distal end of said housing and wherein said second ramp and said first stop are located intermediate said first ramp and said proximal end of said housing.

10. The improved safety syringe of claim 9, wherein each of said third ramp, said fourth ramp, and said second stop is located proximate said distal end of said housing.

11. The improved safety syringe of claim 10, wherein said ring rotates relative to said housing when said first tab slides along said first ramp and said second tab slides along said third ramp, and wherein said ring stops rotating relative to said housing when said second tab engages said second stop after sliding along said third ramp.

12. The improved safety syringe of claim 11, wherein said first tab is axially aligned with said second ramp of said second raised segment when said second tab engages said second stop.

13. The improved safety syringe of claim 12, wherein said urging means urges said first tab to axially engage said second ramp of said second raised segment.

14. The improved safety syringe of claim 13, wherein said ring rotates relative to said housing when said first tab slides along said second ramp of said second raised segment, and wherein said ring stops rotating relative to said housing when said first tab engages said first stop after sliding along said second ramp.

15. The improved safety syringe of claim 14, wherein said second tab is axially aligned with said fourth ramp of said first raised segment when said first tab engages said first stop.

16. The improved safety syringe of claim 15, wherein said first tab is axially aligned with said second groove and said ring is rotated relative to said housing when said second tab slides along said fourth ramp of said first raised segment.

17. In a safety syringe which includes a housing having a bore which extends from a distal end of said housing to a proximal end of said housing; a barrel having a distal end located in said housing and a proximal end located externally of said housing, said barrel being mounted for reciprocating movement within said housing such that said barrel is movable between a retracted position, in which said distal end of said barrel is located proximate said proximal end of said housing, and an extended position, in which said distal end of said barrel is located proximate said distal end of said housing; a needle assembly attached to said barrel at said distal end thereof, said needle assembly having a needle attached thereto; a ring mounted to said barrel about said distal end thereof, said ring being rotatable relative to said housing and to said barrel and including a first tab and a second tab circumferentially spaced from said first tab; and urging means for urging said barrel toward its said retracted position, the improvement wherein said housing has an interior wall which includes first ramp means, positioned so as to be engageable by said first tab, for rotating said ring relative to said housing responsive to the engagement of said first ramp means by said first tab; second ramp means, positioned so as to be engageable by said first tab, for rotating said ring relative to said housing responsive to the engagement of said second ramp means by said first tab; first stop means, positioned so as to be engageable by said first tab, for stopping the rotation of said ring relative to said housing responsive to the engagement of said first stop means by said first tab; third ramp means, positioned so as to be engageable by said second tab, for rotating said ring relative to said housing responsive to the engagement of said third ramp means by said second tab; second stop means, positioned so as to be engageable by said second tab, for stopping the rotation of said ring relative to said housing responsive to the engagement of said second stop means by said second tab; fourth ramp means, positioned so as to be engageable by said second tab, for rotating said ring relative to said housing responsive to the engagement of said fourth ramp means by said second tab; third stop means, positioned so as to be engageable by said first tab, for stopping the rotation of said ring relative to said housing responsive to the engagement of said third stop means by said first tab; and locking means, positioned so as to be engageable by said first tab, for locking said barrel in its said retracted position responsive to the engagement of said locking means by said first tab such that said needle is concealed in said housing.

18. The improved safety syringe of claim 17, wherein said urging means is a compression spring mounted about said barrel such that a substantial portion of said compression spring is located externally of said housing when said barrel is in its said retracted position.

19. The improved safety syringe of claim 18, wherein said barrel includes a flange positioned at said proximal end thereof, said compression spring extending between said flange and said distal end of said barrel.

20. The improved safety syringe of claim 17, further including a plunger mounted for reciprocating movement within said barrel so as to move said barrel to its said extended position.

21. The improved safety syringe of claim 17, wherein said locking means includes a V-shaped notch which is sized and shaped so as to preclude lateral movement of said first tab.

22. The improved safety syringe of claim 17, wherein said interior wall of said housing further includes guiding means for guiding said first tab toward said proximal end of said housing.

23. The improved safety syringe of claim 22, wherein said guiding means includes a lock ramp positioned adjacent said first linear edge.

24. The improved safety syringe of claim 17, wherein said first ramp means is a first angled surface which is sized and shaped so as to allow said first tab to slide therealong.

25. The improved safety syringe of claim 24, wherein said second ramp means is an inclined edge which is sized and shaped so as to allow said first tab to slide therealong.

26. The improved safety syringe of claim 25, wherein said first stop means is a linear edge positioned adjacent said inclined edge.

27. The improved safety syringe of claim 26, wherein said third ramp means is a second angled surface which is sized and shaped so as to allow said second tab to slide therealong.

28. The improved safety syringe of claim 27, wherein said second stop means is a second linear edge positioned adjacent said second angled surface.

29. The improved safety syringe of claim 28, wherein said fourth ramp means is an inclined surface which is sized and shaped so as to allow said second tab to slide therealong.

30. The improved safety syringe of claim 29, wherein said third stop means is a linear wall extending from said proximal end of said housing to said distal end of said housing.

31. The improved safety syringe of claim 30, wherein said first angled surface is located proximate said distal end of said housing and wherein said inclined edge and said first linear edge are located intermediate said first angled surface and said proximal end of said housing.

32. The improved safety syringe of claim 31, wherein each of said second angled surface, said inclined surface, and said second linear edge is located proximate said distal end of said housing.

33. The improved safety syringe of claim 32, wherein said ring rotates relative to said housing when said first tab slides along said first angled surface and said second tab slides along said second angled surface, and wherein said ring stops rotating relative to said housing when said second tab engages said second linear edge after sliding along said second angled surface.

34. The improved safety syringe of claim 33, wherein said first tab is axially aligned with said inclined edge when said second tab engages said second linear edge.

35. The improved safety syringe of claim 34, wherein said urging means urges said first tab to axially engage said inclined edge.

36. The improved safety syringe of claim 35, wherein said ring rotates relative to said housing when said first tab slides along said inclined edge, and wherein said ring stops rotating relative to said housing when said first tab engages said first linear edge after sliding along said inclined edge.

37. The improved safety syringe of claim 36, wherein said second tab is axially aligned with said inclined surface when said first tab engages said linear wall.

38. The improved safety syringe of claim 37, wherein said first tab is axially aligned with said second groove and said ring is rotated relative to said housing when said second tab slides along said inclined surface.

* * * * *